US012690943B2

(12) United States Patent
Mucilli et al.

(10) Patent No.: US 12,690,943 B2
(45) Date of Patent: Jul. 28, 2026

(54) SURGICAL INVENTORY SYSTEMS

(71) Applicant: Covidien LP, Mansfield, MA (US)

(72) Inventors: Jason M. Mucilli, Lakewood, CO (US); Edward L. Brannan, Erie, CO (US); Richard L. Croft, Mead, CO (US); Jennifer M. Layton, Broomfield, CO (US); Benjamin J. Noe, Erie, CO (US); Anthony V. Locatelli, Longmont, CO (US)

(73) Assignee: Covidien LP, Mansfield, MA (US)

( * ) Notice: Subject to any disclaimer, the term of this patent is extended or adjusted under 35 U.S.C. 154(b) by 276 days.

(21) Appl. No.: 18/568,627

(22) PCT Filed: May 11, 2022

(86) PCT No.: PCT/US2022/028681
§ 371 (c)(1),
(2) Date: Dec. 8, 2023

(87) PCT Pub. No.: WO2022/260818
PCT Pub. Date: Dec. 15, 2022

(65) Prior Publication Data
US 2025/0120788 A1        Apr. 17, 2025

Related U.S. Application Data

(60) Provisional application No. 63/209,476, filed on Jun. 11, 2021, provisional application No. 63/209,474, filed on Jun. 11, 2021.

(51) Int. Cl.
*A61B 90/98*        (2016.01)
*A61B 34/20*        (2016.01)
(Continued)

(52) U.S. Cl.
CPC .............. *A61B 90/98* (2016.02); *A61B 34/20* (2016.02); *G01V 15/00* (2013.01);
(Continued)

(58) Field of Classification Search
CPC . A61B 90/98; A61B 34/20; A61B 2034/2051; A61B 2034/2055;
(Continued)

(56) References Cited

U.S. PATENT DOCUMENTS

| | | | |
|---|---|---|---|
| 2017/0020625 A1 | 1/2017 | Bowlsbey et al. | |
| 2020/0289206 A1* | 9/2020 | Rosinski | ............... A61B 34/76 |
| 2021/0052342 A1 | 2/2021 | Rosinski | |

FOREIGN PATENT DOCUMENTS

| | | | | |
|---|---|---|---|---|
| CN | 113143462 A | * | 7/2021 | ............. A61B 34/20 |
| DE | 202009006971 U1 | | 8/2009 | |

OTHER PUBLICATIONS

International Search Report and Written Opinion for International Application No. PCT/US2022/028681 dated Sep. 9, 2022 (9 pages).

* cited by examiner

*Primary Examiner* — An T Nguyen
(74) *Attorney, Agent, or Firm* — Carter, DeLuca & Farrell, LLP

(57)        ABSTRACT

An inventory system configured for reducing variability in detecting and counting surgical items includes an RFID tag affixed to a surgical item, a signal generator configured to generate an energizing signal for the RFID tag, an antenna operably coupled to the signal generator, a sensor configured to generate a signal indicative of a spatial parameter of the antenna when scanning for the RFID tag, a processor, and a memory. The RFID tag is configured to transmit a return signal when energized. The antenna is configured to receive the return signal transmitted by the RFID tag. The memory includes instructions stored thereon, which when executed
(Continued)

by the processor cause the system to scan for the RFID tag by the antenna, sense the signal over a period of time, and provide an indication that the spatial parameter of the antenna over time meets a predetermined rule.

18 Claims, 8 Drawing Sheets

(51) Int. Cl.
　　*G01V 15/00*　　　　　(2006.01)
　　*A61B 90/00*　　　　　(2016.01)
(52) U.S. Cl.
　　CPC ................. *A61B 2034/2051* (2016.02); *A61B 2034/2055* (2016.02); *A61B 2090/0805* (2016.02)
(58) Field of Classification Search
　　CPC .... A61B 2090/0805; A61B 2034/2048; A61B 2090/061; A61B 2090/0818; A61B 90/90; G01V 15/00; G01V 8/10
　　See application file for complete search history.

SURGICAL INVENTORY SYSTEMS

CROSS REFERENCE TO RELATED APPLICATIONS

The present application is a national stage application of International Patent Application No. PCT/US2022/028681, filed May 11, 2022, which claims the benefit of and priority to U.S. Provisional Application Nos. 63/209,474 and 63/209,476, filed on Jun. 11, 2021. Each of the foregoing applications is hereby incorporated by reference in its entirety.

FIELD

The present disclosure relates generally to interrogation and detection systems for radio-frequency (RF) ID tags, and more particularly, reducing variability in detection and inventory systems for potentially retained surgical items within surgical sites.

BACKGROUND

It is often useful to determine whether objects associated with a surgery are present in a patient's body before completion of the surgery. Such objects may take a variety of forms. For example, the objects may take the form of instruments, for instance, scalpels, scissors, forceps, hemostats, and/or clamps. Also, for example, the objects may take the form of related accessories and/or disposable objects, for instance, surgical sponges, gauzes, and/or pads. Failure to locate an object before closing the patient may require additional surgery, and in some instances, may have unintended medical consequences.

Accordingly, there is a need for a technology that is capable of providing both presence detection and tagged surgical item/implement identification functionality in the medical setting, as well as inventory controls of the tagged items/implements. Specifically, detecting the presence of, identifying, and maintaining inventory of tagged surgical items and materials that are used during the execution of a medical procedure. Technologies exist that enable these functions both individually as well as in conjunction with each other, but the methods and packaging of the discrete solutions used are not ideal for the application. More specifically, the components attached or affixed to the items being tracked are either too large physically and present nuisances or obstacles in the execution of the procedure, or the detection and identification performance of the solution may degrade rapidly in the presence of variable and uncontrolled dielectric or conductive materials.

Accordingly, there are needs for improvements in presence detection, tagged item identification, and inventory functionality in the medical setting.

SUMMARY

This disclosure relates to systems for detection of surgical objects and/or devices used in body cavities during surgery, specifically systems that include an antenna to be inserted directly on top of or over a surgical site to detect such surgical objects and/or devices.

In accordance with aspects of the disclosure, an inventory system configured for reducing variability in detecting and counting surgical items includes an RFID tag affixed to a surgical item, a signal generator configured to generate an energizing signal for the RFID tag, an antenna operably coupled to the signal generator, a sensor configured to generate a signal indicative of a spatial parameter of the antenna when scanning for the RFID tag, a processor, and a memory. The antenna is configured to receive the return signal transmitted by the RFID tag. The RFID tag is configured to transmit a return signal when energized. The memory includes instructions stored thereon, which when executed by the processor cause the system to scan, using the antenna, for the RFID tag, sense, by the sensor, the signal indicative of a spatial parameter of the antenna over a period of time, and provide an indication that the spatial parameter of the antenna over time meets a predetermined rule.

In an aspect of the present disclosure, the sensor may include a proximity sensor, a gyro, an accelerometer, a laser sensor, and/or a sensor configured to detect an electronic marker.

In another aspect of the present disclosure, the spatial parameter may include a proximity of the antenna to a patient.

In yet another aspect of the present disclosure, the sensor may be further configured to interpret motion.

In a further aspect of the present disclosure, the instructions, when executed by the processor, may further cause the system to determine if the antenna was moved in a predetermined scanning pattern based on the sensed spatial parameter over the period of time and provide an indication that the antenna was moved in the predetermined scanning pattern based on the determination.

In yet a further aspect of the present disclosure, the instructions, when executed by the processor, may further cause the system to: determine if at least one of a velocity or a speed of motion of the antenna was within a predetermined window based on the sensed spatial parameter over the period of time and provide an indication that the at least one of a velocity or the speed of motion of the antenna was within a predetermined window based on the determination.

In an aspect of the present disclosure, the system may further include a light source configured to project a pattern of visible light on a patient, the pattern configured to indicate a proximity of the antenna to the patient.

In yet another aspect of the present disclosure, the system may further include a surgical table, including a runner configured as a mounting point for the antenna, wherein the antenna is slidably disposed on the runner of the surgical table to enable a clinician the ability to slide the antenna a length of the surgical table while scanning for RFID tags.

In a further aspect of the present disclosure, the scanning may be performed for a predetermined period of time.

In yet a further aspect of the present disclosure, the antenna may include at least two coils. The instructions, when executed by the processor, further cause the system to determine the spatial parameter of the antenna over a period of time based on the at least two coils.

In accordance with aspects of the disclosure, a computer-implemented method for reducing variability in detecting and counting surgical items, includes scanning, using an antenna, for an RFID tag, wherein the antenna is configured to receive a return signal transmitted by the RFID tag, sensing, by a sensor, a signal indicative of a spatial parameter of an antenna over a period of time, wherein the sensor is configured to generate a signal indicative of a spatial parameter of the antenna when scanning for the RFID tag, and provide an indication that the spatial parameter of the antenna over time meets a predetermined rule.

In an aspect of the present disclosure, the sensor may include at least one of a proximity sensor, a gyro, an accelerometer, a laser sensor, or a sensor configured to detect an electronic marker.

In another aspect of the present disclosure, the spatial parameter may include a proximity of the antenna to a patient.

In yet another aspect of the present disclosure, the sensor may be further configured to interpret motion.

In a further aspect of the present disclosure, the method may further include determining if the antenna was moved in a predetermined scanning pattern based on the sensed spatial parameter over the period of time and provide an indication that the antenna was moved in the predetermined scanning pattern based on the determination.

In yet a further aspect of the present disclosure, the method may further include determining if at least one of a velocity or a speed of motion of the antenna was within a predetermined window based on the sensed spatial parameter over the period of time and providing an indication that the at least one of a velocity or the speed of motion of the antenna was within a predetermined window based on the determination.

In an aspect of the present disclosure, the method may further include projecting a pattern of visible light on a patient by a light source, the pattern configured to indicate a proximity of the antenna to the patient.

In accordance with aspects of the disclosure, the scanning may be performed for a predetermined period of time.

In yet a further aspect of the present disclosure, the antenna may include at least two coils. The computer-implemented method may further include determining the spatial parameter of the antenna over a period of time based on the at least two coils.

In an aspect of the present disclosure, a non-transitory computer-readable storage medium in which is stored instructions for causing a processor to execute a computer-implemented method for reducing variability in detecting and counting surgical items, the method includes scanning, using an antenna, for an RFID tag, wherein the antenna is configured to receive a return signal transmitted by the RFID tag, sensing, by a sensor, a signal indicative of a spatial parameter of an antenna over a period of time, wherein the sensor is configured to generate a signal indicative of a spatial parameter of the antenna when scanning for the RFID tag, and provide an indication that the spatial parameter of the antenna over time meets a predetermined rule.

In accordance with aspects of the disclosure, an inventory system configured for reducing variability in detecting and counting surgical items, includes an RFID tag affixed to a surgical item, a signal generator configured to generate an energizing signal for the RFID tag, a scanning peripheral configured to receive the return signal transmitted by the RFID tag, a sensor configured to generate a signal indicative of a spatial parameter of the scanning peripheral when scanning for the RFID tag, a processor, and a memory. The RFID tag is configured to transmit a return signal when energized. The memory includes instructions stored thereon, which when executed by the processor cause the system to receive patient data from an electronic medical record (EMR), determine a parameter of a scanning procedure based on the patient data, verify the parameter of the scanning procedure based on the sensor, and provide an indication that the parameter of the scanning procedure was verified.

In an aspect of the present disclosure, the patient data may include a surgical procedure and/or a patient physical characteristic.

In another aspect of the present disclosure, the parameter of the scanning procedure may include a scanning pattern, the selection of the scanning peripheral, and/or a power level.

In yet another aspect of the present disclosure, the scanning peripheral may include a hand-held first antenna operably coupled to the signal generator and/or a second antenna integrated into a surgical table. In a case where the parameter of the scanning procedure is the selection of the scanning peripheral, the instructions when executed by the processor further cause the system to determine if scanning should be performed based on the hand-held antenna and/or the antenna integrated into a surgical table, based on the patient data, scan, using the determined hand-held antenna and/or the determined second antenna, for the RFID tag, sense, by the sensor, a signal indicative of a spatial parameter of the scanning peripheral over a period of time, determine if the spatial parameter over time meets a predetermined rule, and provide an indication that the spatial parameter over time meets the recommended scanning pattern.

In a further aspect of the present disclosure, in a case where the parameter of the scanning procedure is the scanning pattern, the instructions, when executed by the processor, may further cause the system to recommend the scanning pattern based on the surgical procedure in the EMR and display on a display the recommended scanning pattern.

In yet a further aspect of the present disclosure, the instructions, when executed by the processor, may further cause the system to: scan, using an antenna, for an RFID tag, wherein the antenna is configured to receive a return signal transmitted by the RFID tag; sense, by a sensor, a signal indicative of a spatial parameter of an antenna over a period of time, wherein the sensor is configured to generate a signal indicative of a spatial parameter of the antenna when scanning for the RFID tag; determine if the spatial parameter over time meets the recommended scanning pattern; and provide an indication that the spatial parameter over time meets the recommended scanning pattern.

In an aspect of the present disclosure, the sensor may include at least one of a proximity sensor, a gyro, an accelerometer, a laser sensor, or a sensor configured to detect an electronic marker.

In another aspect of the present disclosure, the system may further include a light source configured to project a pattern of visible light on a patient, the pattern configured to indicate a proximity of the antenna to the patient.

In yet another aspect of the present disclosure, the system may further include a surgical table, including a runner configured as a mounting point for the first antenna, wherein the first antenna is slidably disposed on the runner of the surgical table to enable a clinician the ability to slide the first antenna a length of the surgical table while scanning for RFID tags.

In a further aspect of the present disclosure, the sensor may further be configured to interpret motion.

In an aspect of the present disclosure, a computer-implemented method for reducing variability in detecting and counting surgical items, includes receiving patient data from an electronic medical record (EMR), determining a parameter of a scanning procedure based on the patient data, verifying the parameter of the scanning procedure, and providing an indication that the parameter of the scanning procedure was verified.

In another aspect of the present disclosure, the patient data may include a surgical procedure and/or a patient physical characteristic.

In yet another aspect of the present disclosure, the parameter of the scanning procedure may include at least one of a scanning pattern, a scanning peripheral, and/or a power level.

In a further aspect of the present disclosure, in a case where the parameter of the scanning procedure is the scanning peripheral, the method may further include determining if scanning should be performed based on a first hand-held antenna and/or a second antenna integrated into a surgical table, based on the patient data, scanning, using the determined first antenna and/or the determined second antenna, for an RFID tag, wherein the first antenna and the second antenna are configured to receive a return signal transmitted by the RFID tag, sensing, by a sensor, a signal indicative of a spatial parameter of the first antenna and/or the second antenna over a period of time, wherein the sensor is configured to generate a signal indicative of a spatial parameter of the antenna when scanning for the RFID tag, determining if the spatial parameter over time meets a predetermined rule, and providing an indication that the spatial parameter over time meets the recommended scanning pattern.

In yet a further aspect of the present disclosure, in a case where the parameter of the scanning procedure is the scanning pattern, the method may further include recommending the scanning pattern based on the surgical procedure in the EMR and displaying the recommended scanning pattern on a display.

In an aspect of the present disclosure, the method may further include scanning, using a hand-held first antenna, for an RFID tag, wherein the first antenna is configured to receive a return signal transmitted by the RFID tag, sensing, by a sensor, a signal indicative of a spatial parameter of the first antenna over a period of time, wherein the sensor is configured to generate a signal indicative of a spatial parameter of the first antenna when scanning for the RFID tag, determining if the spatial parameter over time meets the recommended scanning pattern, and providing an indication that the spatial parameter over time meets the recommended scanning pattern.

In another aspect of the present disclosure, the sensor may include at least one of a proximity sensor, a gyro, an accelerometer, a laser sensor, or a sensor configured to detect an electronic marker.

In yet another aspect of the present disclosure, the spatial parameter may include a proximity of the antenna to a patient.

In a further aspect of the present disclosure, the sensor may further be configured to interpret motion.

In yet a further aspect of the present disclosure, a non-transitory computer-readable storage medium in which is stored instructions for causing a processor to execute a computer-implemented method for reducing variability in detecting and counting surgical items, the method includes receiving patient data from an electronic medical record, determining a parameter of a scanning procedure based on the patient data, verifying the parameter of the scanning procedure, and providing an indication that the parameter of the scanning procedure was verified.

BRIEF DESCRIPTION OF THE DRAWINGS

In the drawings, identical reference numbers identify similar elements or acts. The sizes and relative positions of elements in the drawings are not necessarily drawn to scale.

For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements and have been solely selected for ease of recognition in the drawings.

Various aspects of the presently disclosed antennae, RF tags, and articles containing them are described hereinbelow with reference to the drawings.

Figure 1:
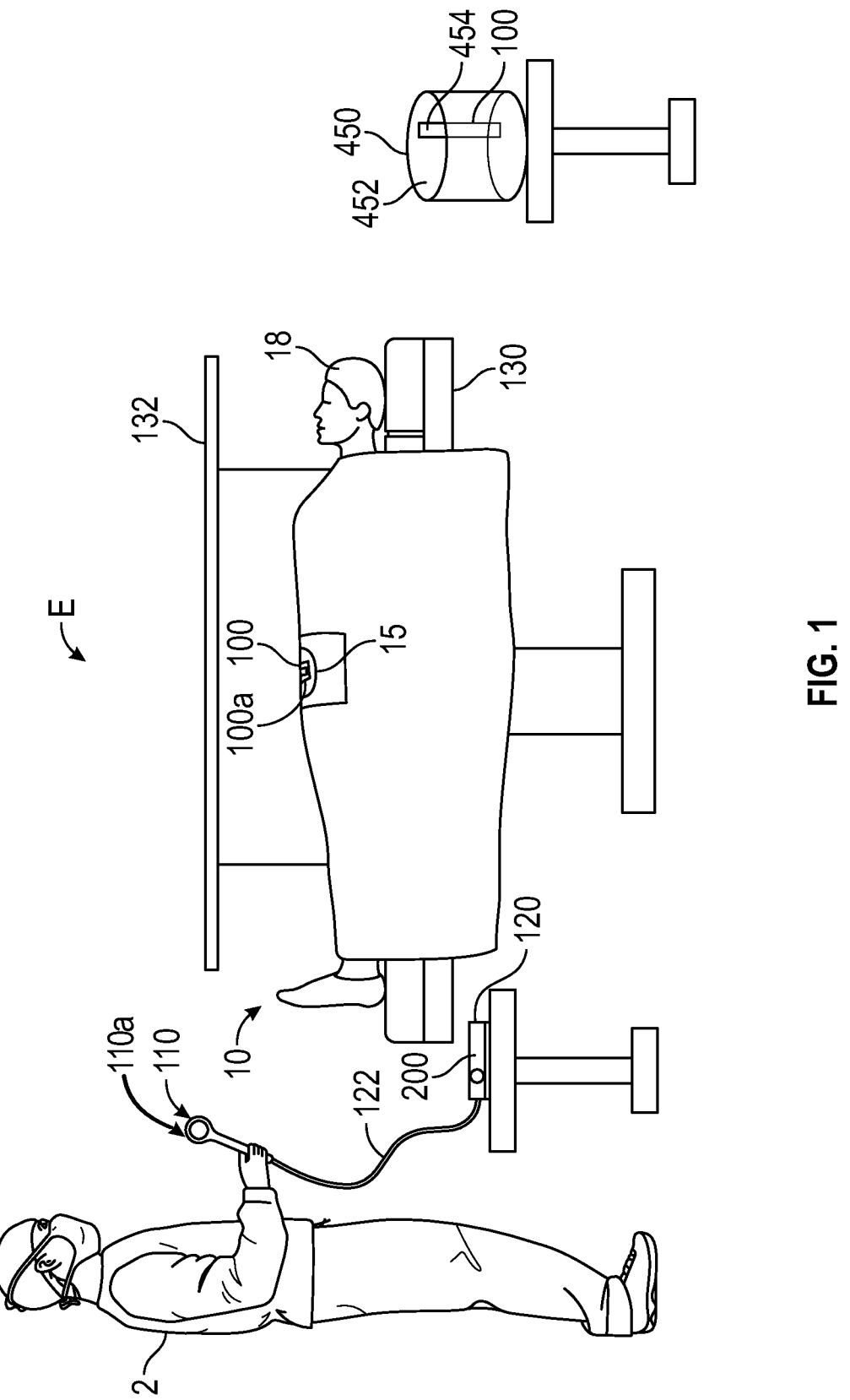
Figure 2:
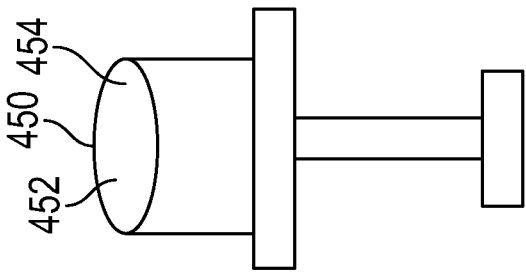
Figure 2:
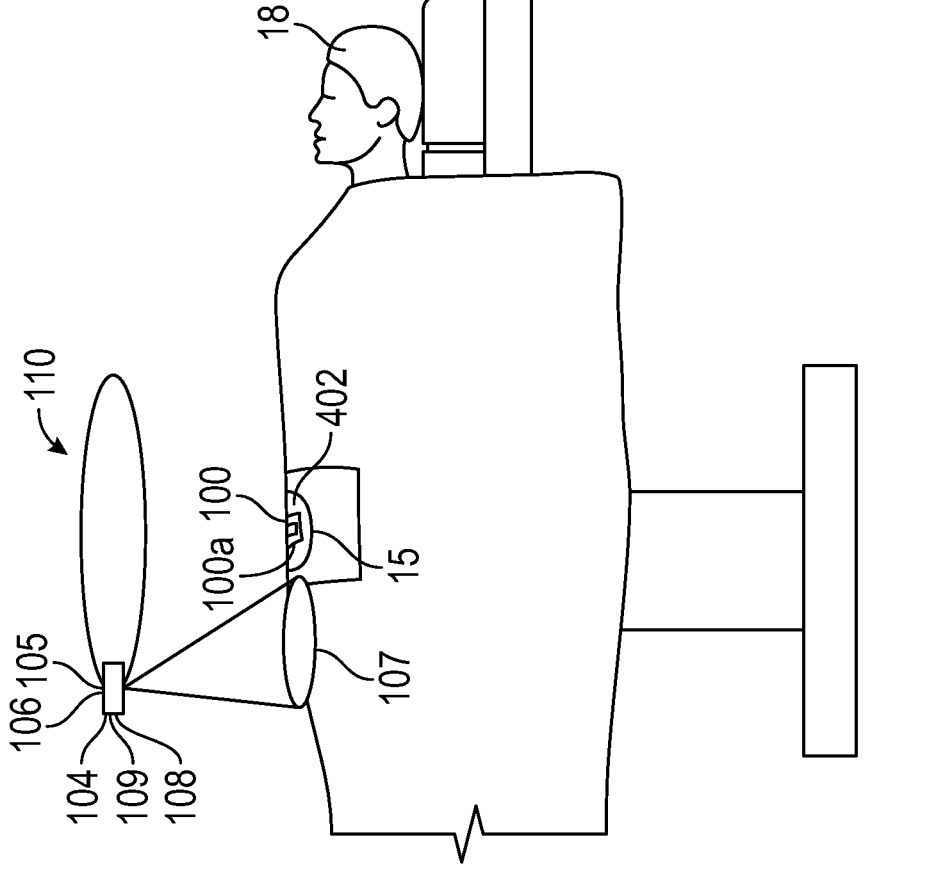
Figure 3:
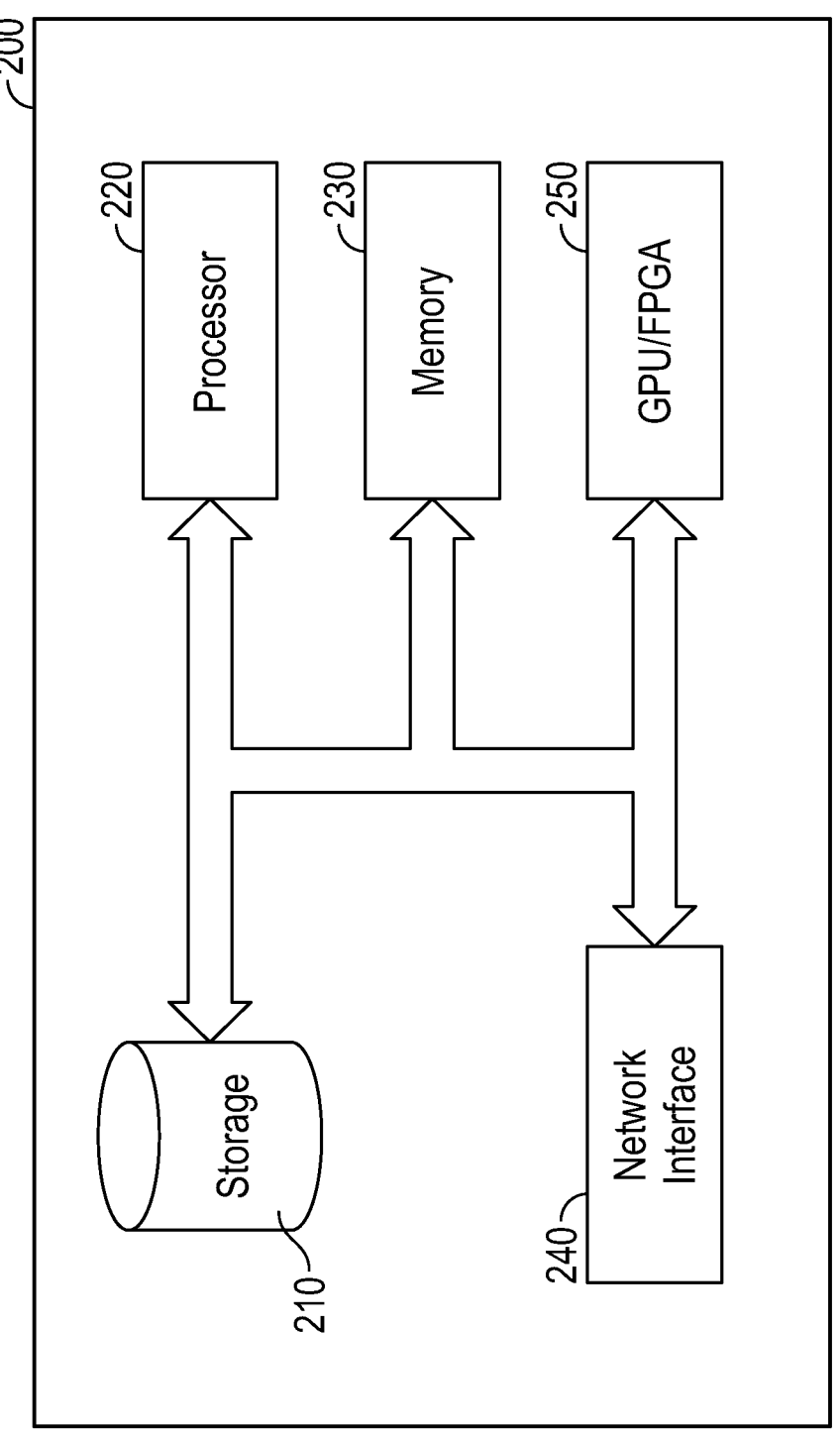
Figure 4:
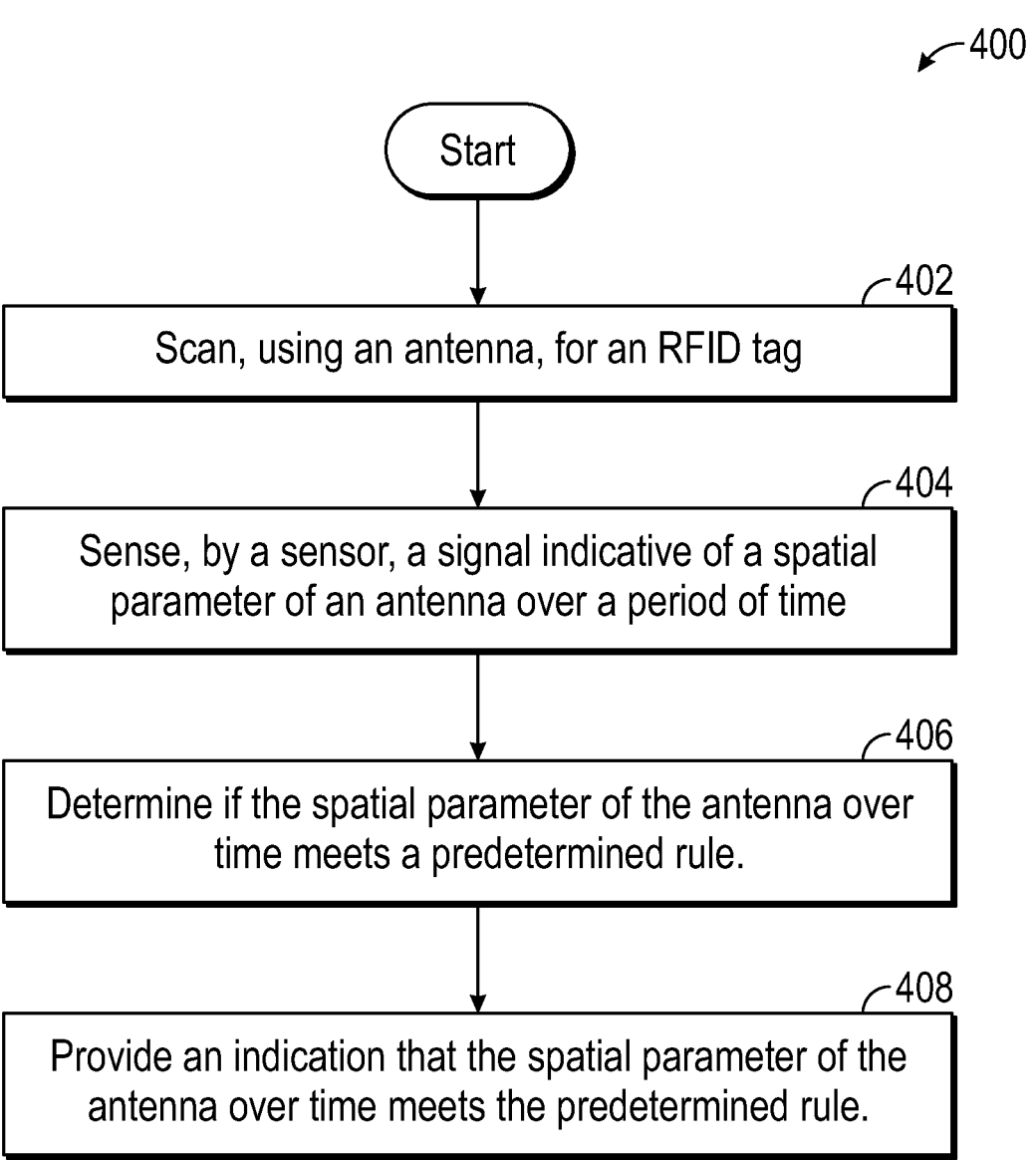
Figure 5:
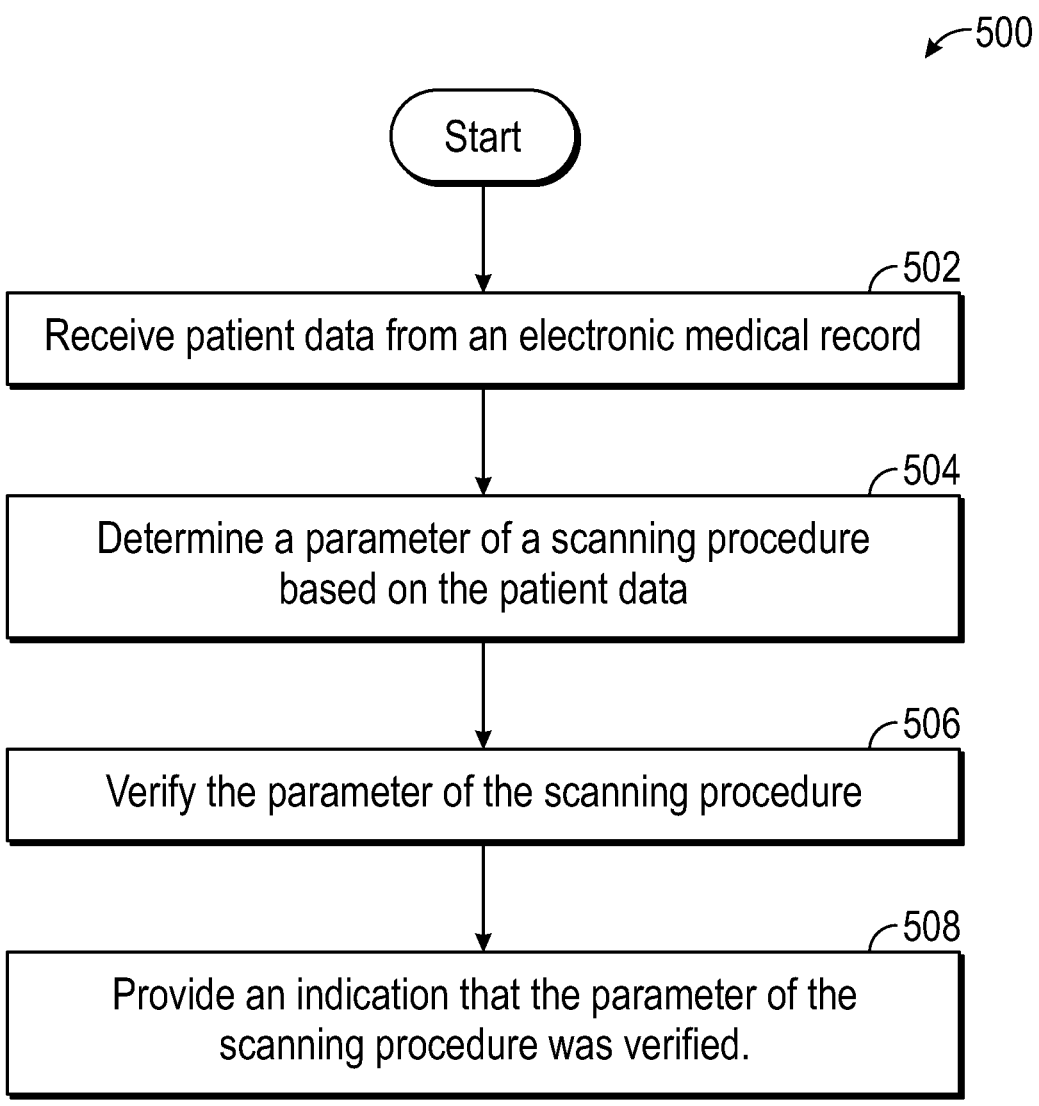
Figure 6:
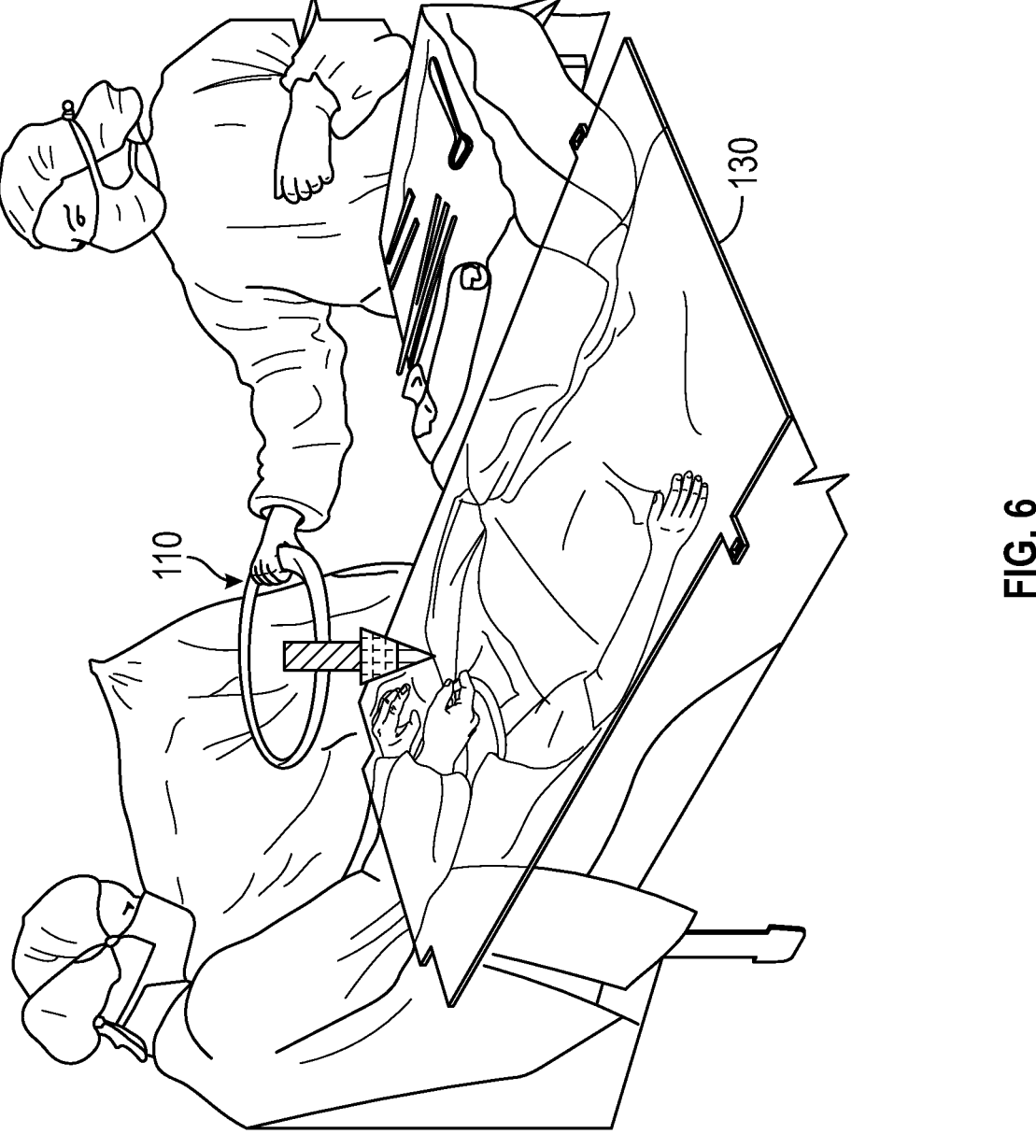
Figure 7:
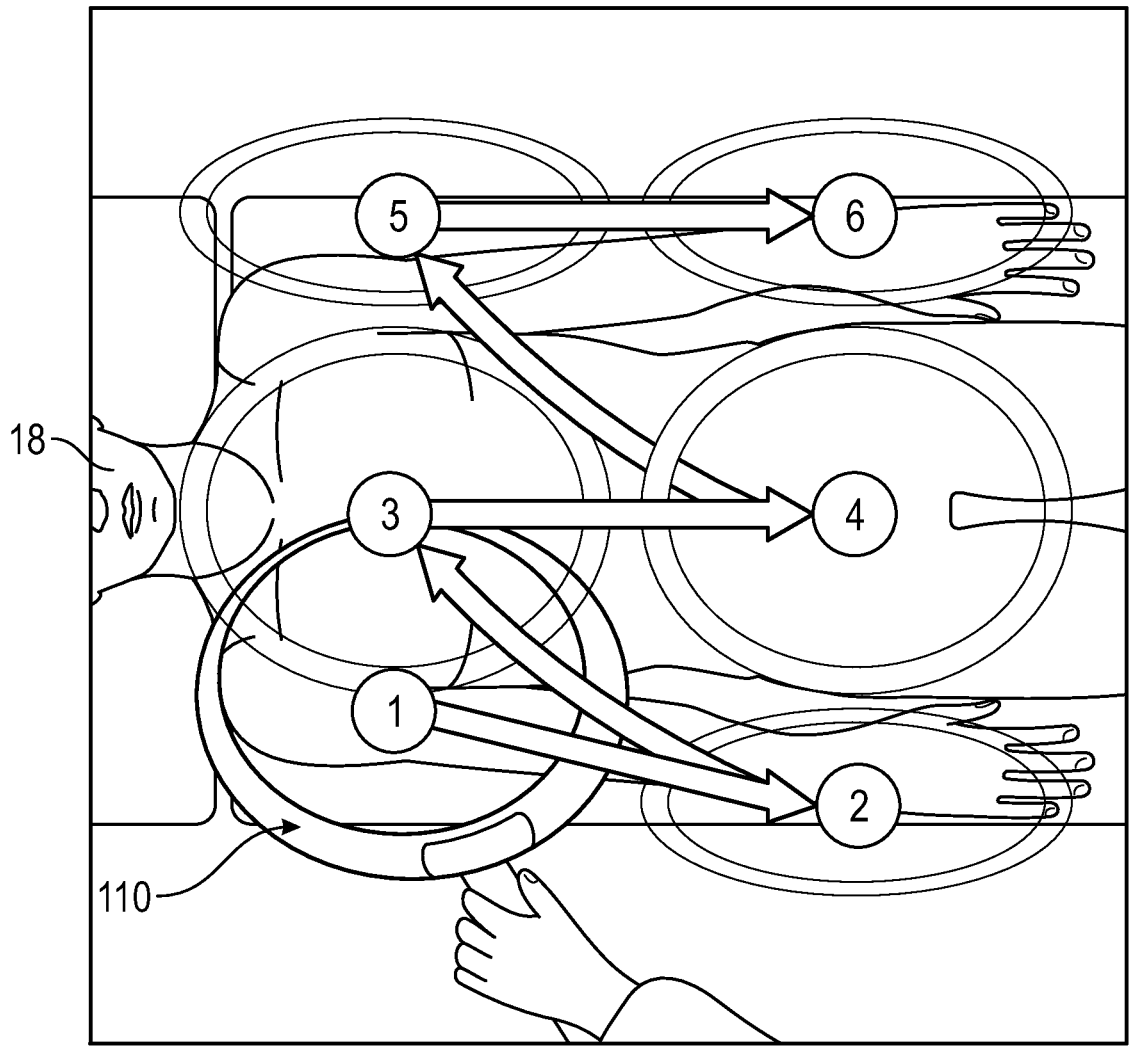
Figure 8:
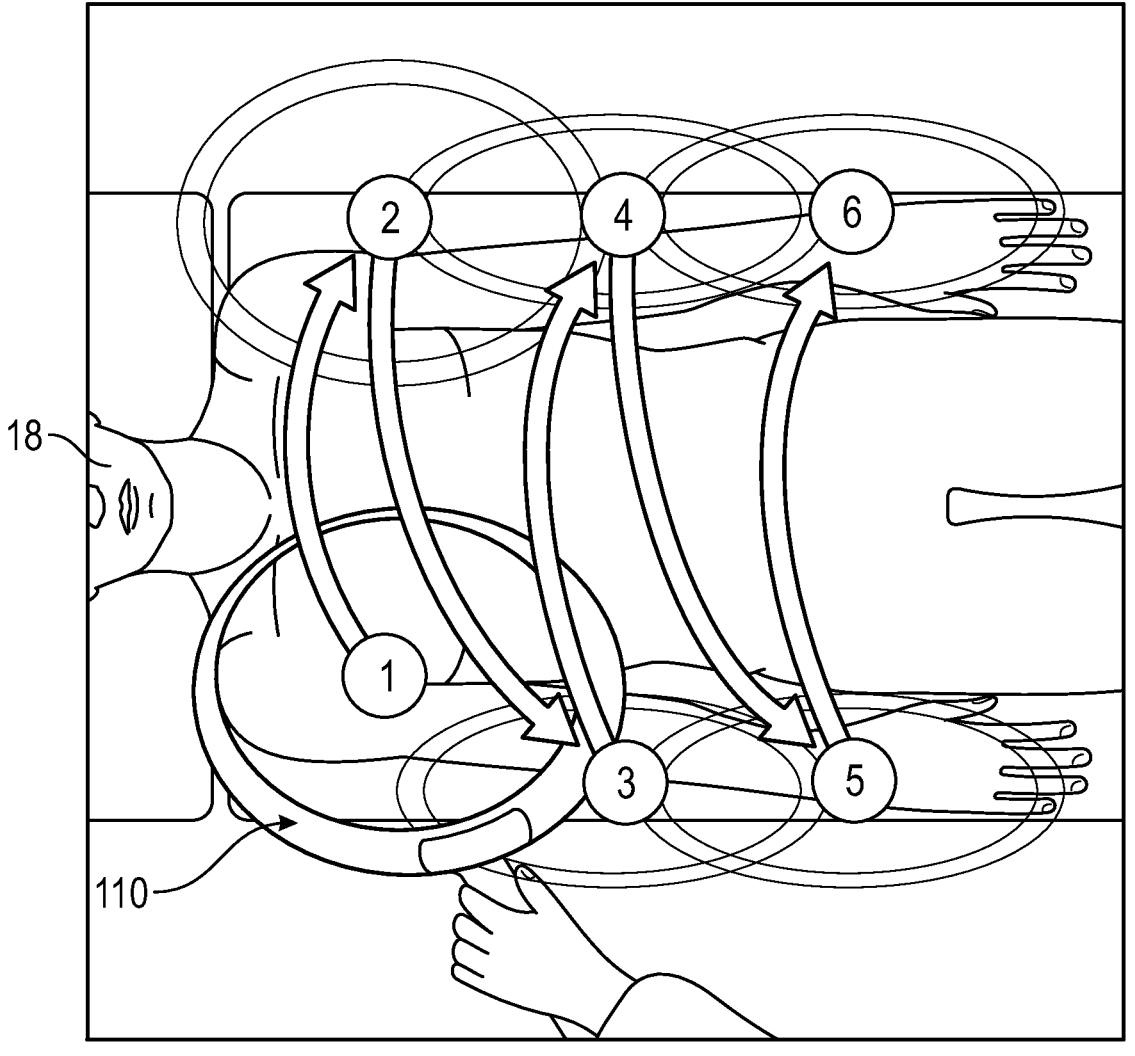

FIG. 1 is a schematic diagram showing a surgical environment illustrating a clinician using an inventory system for detecting and counting an object within a patient that is tagged with an RFID tag according to one illustrated aspect;

FIG. 2 is a schematic illustration of an antenna for detection of surgical implements within a patient's body in active use within a surgical site;

FIG. 3 is a block diagram of a controller of the system of FIG. 1;

FIG. 4 is a flow chart of a computer-controlled method for detecting and counting potentially retained surgical items using the system of FIG. 1;

FIG. 5 is a flow chart of a computer-controlled method for detecting and counting potentially retained surgical items using the system of FIG. 1;

FIG. 6 is a schematic diagram showing a surgical environment illustrating a clinician using an inventory system for detecting and counting an object within a patient that is tagged with an RFID tag according to one illustrated aspect;

FIG. 7 is a schematic diagram showing a 'W' scanning pattern according to one illustrated aspect; and FIG. 8 is a schematic diagram showing a 'Z' or 'N' scanning pattern according to one illustrated aspect.

DETAILED DESCRIPTION

In the following description, certain specific details are set forth in order to provide a thorough understanding of disclosed aspects. However, one skilled in the relevant art will recognize that aspects may be practiced without one or more of these specific details or with other methods, components, materials, etc. In other instances, well-known structures associated with transmitters, receivers, or transceivers have not been shown or described in detail to avoid unnecessarily obscuring descriptions of the aspects.

Reference throughout this specification to "one aspect" or "an aspect" means that a particular feature, structure, or characteristic described in connection with the aspect is included in at least one aspect. Thus, the appearances of the phrases "in one aspect" or "in an aspect" in various places throughout this specification are not necessarily all referring to the same aspect. Furthermore, the particular features, structures, or characteristics may be combined in any suitable manner in one or more aspects.

FIG. 1 depicts a surgical environment "E" in which a clinician 12 operates an inventory system 10 for detection and counting of radio-frequency identification (RFID) tags to ascertain the presence or absence of items, implements or objects 100a in a patient 18. The inventory system 10 may include a signal generator 120 and an antenna 110 coupled to the signal generator 120 by one or more communication paths, for example, coaxial cable 122. In one aspect of the inventory system 10, the antenna 110 may take the form of a hand-held wand 110a.

In aspects, the antenna 110 may be incorporated in the surgical table 130. The surgical table 130 may include a runner 132 the length of the surgical table 130. The runner 132 is configured as a mounting point for the antenna 110. For example, the antenna 110 may be slidably attached to the runner 132 of the surgical table 130 to enable a clinician 12 the ability to slide the antenna 110 the length of the surgical table 130 while scanning for RFID tags 100.

The object 100a may take a variety of forms, for example, instruments, accessories, and/or disposable objects useful in performing surgical procedures. For instance, the object 100a may take the form of scalpels, scissors, forceps, hemostats, and/or clamps. Also, for example, the objects 100a may take the form of surgical sponges, gauze, and/or padding. The object 100a is tagged, carrying, attached, or otherwise coupled to an RFID tag 100. Aspects of the inventory system 10 disclosed herein are particularly suited to operate with one or more RFID tags 100, which are not accurately tuned to a chosen or selected resonant frequency. Consequently, the RFID tags 100 do not require high manufacturing tolerances or expensive materials and thus may be inexpensive to manufacture.

In use, the clinician 12 may position the wand 110a proximate the patient 18 in order to detect the presence or absence of the one or more RFID tags 100 and hence an object 100a. The clinician 12 may, in some aspects, move the wand 110a along and/or across the body of the patient 18. For a detailed description of an exemplary inventory system, reference may be made to commonly owned U.S. Patent Application Publication No. 2004/0250819, the entire content of which is hereby incorporated by reference herein.

Referring now to FIG. 2, inventory system 10, for detection and counting of surgical implements (e.g., object 100a) within a patient's body, includes a signal generator 120 to provide an energizing signal for one or more RFID tags 100 (FIG. 1) affixed to an object 100a (FIG. 1). Each RFID tag 100 is configured to transmit a return signal when energized, such that an antenna 110 can detect the return signal and confirm the presence of objects 100a within the body of patient 18. The antenna 110 is operably coupled to the signal generator 120 via a communication cable 122 which may be of variable length to provide greater range of motion to the clinician handling the antenna 110. The signal generator 120 may include a controller 200. It is contemplated that the signal generator 120 may wirelessly communicate with the antenna 110.

In one aspect of inventory system 10, the antenna 110 is an antenna 110 configured to be waved over the surgical site 15, e.g., over the body of patient 18. For example, the antenna 110 may be held over the body of the patient 18 at the height of about two inches (FIG. 6) while attempting to detect RFID tags 100 (e.g., first RFID tags 452 and/or second RFID tags 100), so that the user may detect the presence of objects 100a within the body of patient 18.

The antenna 110 may include a gyro sensor 104 (e.g., an angular rate sensor) configured to sense the angular velocity of the antenna 110 and/or an accelerometer configured to measure the movement of the antenna 110. For example, the gyro sensor 104 and/or the accelerometer 106 may be used by the controller 200 to interpret motion of the antenna 110. The interpreted motion may be used to verify that specific vertical and horizontal scan patterns are used by a clinician 12, (e.g., a 'W' or 'Z'/'N' pattern). See FIG. 7 for an example 'W' scanning pattern and FIG. 8 for an example, 'Z'/'N' scanning pattern. In aspects, the controller 200 may determine if either a velocity and/or a speed of the antenna 110 exceeds a predetermined minimum or maximum limit (e.g., about 15.2 cm/s) based on the interpreted motion. In aspects, the controller 200 may determine whether or not the antenna 110 is properly oriented.

In aspects, the antenna 110 may include a proximity sensor 105 and or a laser distance sensor 109 configured to generate a signal indicating a distance between a patient and the antenna 110. For example, the controller 200 may receive the signal indicating the distance between the antenna 110 and the patient 18 and determine that the antenna 110 is too close to the patient 18. In aspects, the controller 200 may provide an audio and/or visual indication to aid the clinician 12 in using the antenna 110. For example, if the controller 200 determines that the antenna 110 is too close (or too far) to a patient 18, the controller 200 may cause the inventory system 10 (FIG. 1) to emit a tone, warning the clinician 12 that the antenna 110 is outside of an optimal scanning distance.

In aspects, the antenna 110 may include a light source 108 configured to project a visual motif 107, such as a pattern, converging crosshairs, and/or a Medtronic® walking man or other logo (Medtronic, Inc., Minneapolis, MN). For example, the light source 108 may project the visual motif 107 on the patient 18 and be instructed by the controller 200 to use the visual motif 107 to visualize "painting" the patient 18 or surgical site with the projected light, covering all areas of concern.

In aspects, the controller 200 may determine if a scan was performed for a predetermined minimum amount of time, based on a timer. For example, the controller 200, may determine that the antenna 110 was scanning for about 5 seconds. If the predetermined minimum amount of time is 60 seconds, then the controller 200 may emit a visual and/audio alert warning the clinician 12 that the scan was too short and needs to be longer.

FIG. 3 illustrates that controller 200 includes a processor 220 connected to a computer-readable storage medium or a memory 230. The computer-readable storage medium or memory 230 may be a volatile type of memory, e.g., RAM, or a non-volatile type of memory, e.g., flash media, disk media, etc. In various aspects of the disclosure, the processor 220 may be another type of processor such as, without limitation, a digital signal processor, a microprocessor, an ASIC, a graphics processing unit (GPU), a field-programmable gate array (FPGA), or a central processing unit (CPU). In certain aspects of the disclosure, network inference may also be accomplished in systems that have weights implemented as memristors, chemically, or other inference calculations, as opposed to processors.

In aspects of the disclosure, the memory 230 can be random access memory, read-only memory, magnetic disk memory, solid-state memory, optical disc memory, and/or another type of memory. In some aspects of the disclosure, the memory 230 can be separate from the controller 200 and can communicate with the processor 220 through communication buses of a circuit board and/or through communication cables such as serial ATA cables or other types of cables. The memory 230 includes computer-readable instructions that are executable by the processor 220 to operate the controller 200. In other aspects of the disclosure, the controller 200 may include a network interface 240 to communicate with other computers or to a server. A storage device 210 may be used for storing data.

Referring to FIG. 4, there is shown a flow chart of an exemplary computer-implemented method 400 for reducing variability in detecting and counting surgical items within surgical sites in accordance with aspects of the present disclosure. Although the steps of FIG. 4 are shown in a particular order, the steps need not all be performed in the specified order, and certain steps can be performed in another order. For simplicity, FIG. 4 will be described below, with the controller 200 performing the operations. However, in various aspects, the operations of FIG. 4 may be performed in part by the controller 200 of FIG. 3 and in part by another device, such as a remote server. These variations are contemplated to be within the scope of the present disclosure.

Initially at step 402, the controller scans, using an antenna, for an RFID tag. The antenna is configured to receive a return signal transmitted by the RFID tag.

In aspects, the controller may project a pattern of visible light on a patient by a light source on the area to be scanned. For example, the pattern may be configured to indicate a proximity of the antenna 110 to the patient.

Next, at step 404, the controller senses, by a sensor, a signal indicative of a spatial parameter of an antenna 110 over a period of time. The sensor may include a proximity sensor, a gyro 104, an accelerometer 106, a laser sensor 109, or a sensor configured to detect an electronic marker.

The sensor is configured to generate a signal indicative of a spatial parameter of the antenna when scanning for the RFID tag. The spatial parameter may include a proximity of the antenna to a patient.

In aspects, electronic markers may be incorporated in the surgical table and/or in sterile drapes so that the clinician has to "hit" each target marker in order for a scan to be completed. For example, the markers may illuminate once scanned.

In aspects, the sensor may further interpret motion (e.g., motion of the antenna relative to the surgical table, including vertical motion such as up and/or down, and/or horizontal motion).

Next, at step 406, the controller determines if the spatial parameter of the antenna over time meets a predetermined rule. For example, the predetermined rule may include verification that specific antenna scan patterns were used ('W' or 'Z'/'N' pattern), verification that the velocity/speed of motion of the antenna did not exceed a maximum or minimum limit, verification that the antenna is oriented properly (e.g., parallel to the patient), and/or verification that the antenna is close enough to the patient.

Next, at step 408, the controller provides an indication that the spatial parameter of the antenna over time meets the predetermined rule. For example, the controller may determine if a velocity or a speed of motion of the antenna was within a predetermined window based on the sensed spatial parameter over the period of time and the controller may provide an indication that the velocity or the speed of motion of the antenna was within a predetermined window based on the determination.

In aspects, the controller may determine if the antenna was moved in a predetermined scanning pattern based on the sensed spatial parameter over the period of time. The controller may provide an indication that the antenna was moved in the predetermined scanning pattern based on the determination. The scanning may be performed for a predetermined period of time (e.g., about ten minutes).

Thus, the system may verify that the clinicians are not only are utilizing proper scanning technique but also that they are scanning for a minimum pre-defined time. Only when the clinician meets both criteria will a scan complete be possible. In aspects, the system may provide an audible indication (such as an audible tick) to tell the clinician how long each individual scanning pass should be.

In aspects, the antenna may include two or more coils. The controller may determine the spatial parameter of the antenna over a period of time, based on the two or more coils.

In aspects, the clinician may initiate a scan, using a terminal/console, an activation button on the antenna, which can either be pressed once to activate or require the button to be pressed for the entirety of the scan; and/or sound activation. For example, the clinician may say out loud "Begin Scan."

In aspects, the system may alert the clinician and provide troubleshooting feedback (audible and/or visual) to warn and train the clinician of proper/improper use or to help locate a missing sponge/tag. For example, an alert is triggered when the scanning peripheral gets closer to a sponge/tag. In another example, the audio signal (or a plurality of LEDs showing detection strength) may increase in volume and/or frequency as the wand gets closer to the object to aid in locating the object (such as when the object is outside of the body). In another example, an alert can help pinpoint an exact location by indicating a last known location of a sponge/tag that was detected by the antenna, such as a light that illuminates in the direction of the last known "detection" point or a signal strength indicator. In yet another example, the system may include a visual display of the scanned field and the 'completeness' of the scan in a given spatial location coupled with an elapsed time of scan.

The system may include an antenna 110 integrated in the surgical table 130 (or integrates into a surgical table's mattress and/or a mat that is placed on top of the surgical table's mattress) (e.g., to cover the entire surgical site). The antenna 110 could be put into a continuous monitoring mode to allow for the clinician to know at any point during the procedure if a sponge is located within the confines of the surgical site. The RFID tag 100 may include additional information such as SKU level information and quantity of sponges located within the confines of the antenna 110.

In aspects, the controller 200 may optimize a retained surgical instrument prevention system algorithm by increasing/decreasing RF power level which is propagated through patient. In aspects, the controller 200 may prevent system interference by integrating a room calibration mode to help cancel out these known sources of interference that could impact the system's ability to solicit an RFID tag 100 response. The controller 200 may actively monitor the scanning peripherals impedance characteristics when a patient or RFID tag 100 is not present to get a baseline reading and then optimize the system algorithm taking this baseline reading into account.

Referring to FIG. 5, there is shown a flow chart of an exemplary computer-implemented method 500 for reducing variability in detecting and counting surgical items within surgical sites in accordance with aspects of the present disclosure. Although the steps of FIG. 5 are shown in a particular order, the steps need not all be performed in the specified order, and certain steps can be performed in another order. For simplicity, FIG. 5 will be described below, with the controller 200 performing the operations. However, in various aspects, the operations of FIG. 5 may be performed in part by the controller 200 of FIG. 3 and in part by another device, such as a remote server. These variations are contemplated to be within the scope of the present disclosure.

Initially, at step 502, the controller 200 receives patient data from an electronic medical record (EMR). An electronic medical record may include an electronic health record (EHR). For example, the controller 200 may access the patient's EMR from the hospital's database.

Next, at step 504, the controller 200 determines a parameter of a scanning procedure based on the patient data. For example, the patient data may include a surgical procedure and/or a patient physical characteristic (e.g., high body mass index). The parameter of the scanning procedure may include a scanning pattern (such as a 'W' or a 'Z'/'N' pattern), a scanning peripheral, and/or a power level (e.g., a maximum range mode, a minimum range mode, or any power level therebetween). In aspects, the scanning peripheral may include a hand-held wand 110a and/or an antenna integrated into a surgical table 110 (or integrates into a surgical table's mattress and/or a mat that is placed on top of the surgical table's mattress), based on the patient data (FIG. 6).

For example, in a case where the parameter of the scanning procedure is the scanning pattern, the controller may recommend a particular scanning pattern based on the surgical procedure in the EMR and displaying the recommended scanning pattern on a display.

For example, if the patient has a high BMI, the controller 200 may determine that both the hand-held wand 110a and the antenna integrated into a surgical table (or integrates into a surgical table's mattress and/or a mat that is placed on top of the surgical table's mattress) be deployed (the hand-held wand 110a to scan up and the antenna integrated into a surgical table (or integrates into a surgical table's mattress and/or a mat that is placed on top of the surgical table's mattress to scan down). In another example, to address high BMI patients, the controller would put the scanning peripherals into a maximum range mode to optimize power delivery for that particular patient.

For example, in a case where the parameter of the scanning procedure is the scanning peripheral, the controller may determine if scanning should be performed based on a first hand-held wand 110a and/or a second antenna 110 integrated into a surgical table 130 (or integrates into a surgical table's mattress and/or a mat that is placed on top of the surgical table's mattress), based on the patient data. The controller may scan, using the determined first antenna and/or the determined second antenna, for an RFID tag 100. Next, the controller may sense, by a sensor, a signal indicative of a spatial parameter of an antenna over a period of time, wherein the sensor is configured to generate a signal indicative of a spatial parameter of the antenna when scanning for the RFID tag 100. The controller may determine if the spatial parameter over time meets a predetermined rule and provide an indication that the spatial parameter over time meets the recommended scanning pattern.

Next, at step 506, the controller 200 verifies the parameter of the scanning procedure. The controller may verify the parameter of the scanning procedure based on the sensor. For example, the sensor may sense the movement of the first antenna to determine that the first antenna was moved in the recommended scanning pattern.

Next, at step 508, the controller 200 provides an indication that the parameter of the scanning procedure was verified. For example, the controller may provide a visual indication on a display, a visual indication using a light such as a green or red LED (indicating passing or failing verification), or an audio indication.

In aspects, the controller may record into the hospital's EMR for documentation and record keeping purposes as well as to inform OR management of staff proper/improper use and which type of scanning peripheral was utilized.

In aspects, the clinician may scan, using a hand-held wand (i.e., a first antenna), for the RFID tag 100. The controller may sense, by a sensor, a signal indicative of a spatial parameter of the first antenna over a period of time. The sensor is configured to generate a signal indicative of a spatial parameter of the first antenna when scanning for the RFID tag 100. For example, the spatial parameter may be the velocity/speed of motion in a particular pattern (such as a 'Z'/'N') of the first antenna. The controller may determine if the spatial parameter over time meets the recommended scanning pattern. The controller may provide an indication that the spatial parameter over time meets the recommended scanning pattern, by displaying a confirmation on a display or by an audio indication such as a voice stating, "scan complete."

While several aspects of the disclosure have been shown in the drawings and/or described herein, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope of the claims appended hereto.

What is claimed is:

1. An inventory system configured for reducing variability in detecting and counting surgical items, the inventory system comprising:
   an RFID tag affixed to a surgical item, the RFID tag configured to transmit a return signal when energized;
   a signal generator configured to generate an energizing signal for the RFID tag;
   an antenna operably coupled to the signal generator, the antenna configured to receive the return signal transmitted by the RFID tag;
   a sensor configured to generate a signal indicative of a spatial parameter of the antenna when scanning for the RFID tag;
   a processor; and
   a memory, including instructions stored thereon, which when executed by the processor cause the system to:
      scan, using the antenna, for the RFID tag;
      sense, by the sensor, the signal indicative of a spatial parameter of the antenna over a period of time;
      provide an indication that the spatial parameter of the antenna over time meets a predetermined rule;
      determine if the antenna was moved in a predetermined scanning pattern based on the sensed spatial parameter over the period of time; and
      provide an indication that the antenna was moved in the predetermined scanning pattern based on the determination.

2. The system of claim 1, wherein the sensor includes at least one of a proximity sensor, a gyro, an accelerometer, a laser sensor, or a sensor configured to detect an electronic marker.

3. The system of claim 2, wherein the spatial parameter includes a proximity of the antenna to a patient.

4. The system of claim 1, wherein the sensor is further configured to interpret motion.

5. The system of claim 4, wherein the instructions, when executed by the processor, further cause the system to:
   determine if at least one of a velocity or a speed of motion of the antenna was within a predetermined window based on the sensed spatial parameter over the period of time; and
   provide an indication that the at least one of a velocity or the speed of motion of the antenna was within a predetermined window based on the determination.

6. The system of claim 1, further comprising a light source configured to project a pattern of visible light on a patient, the pattern configured to indicate a proximity of the antenna to the patient.

7. The system of claim 1, further comprising a surgical table, including a runner configured as a mounting point for the antenna, wherein the antenna is slidably disposed on the runner of the surgical table to enable a clinician the ability to slide the antenna a length of the surgical table while scanning for RFID tags.

8. The system of claim 1, wherein the scanning is performed for a predetermined period of time.

9. The system of claim 1, wherein:

the antenna includes at least two coils, and the instructions, when executed by the processor, further cause the system to determine the spatial parameter of the antenna over a period of time based on the at least two coils.

10. A computer-implemented method for reducing variability in detecting and counting surgical items, comprises:

scanning, using an antenna, for an RFID tag, wherein the antenna is configured to receive a return signal transmitted by the RFID tag;

sensing, by a sensor, a signal indicative of a spatial parameter of an antenna over a period of time, wherein the sensor is configured to generate a signal indicative of a spatial parameter of the antenna when scanning for the RFID tag;

providing an indication that the spatial parameter of the antenna over time meets a predetermined rule;

determining if the antenna was moved in a predetermined scanning pattern based on the sensed spatial parameter over the period of time; and providing an indication that the antenna was moved in the predetermined scanning pattern based on the determination.

11. The computer-implemented method of claim 10, wherein the sensor includes at least one of a proximity sensor, a gyro, an accelerometer, a laser sensor, or a sensor configured to detect an electronic marker.

12. The computer-implemented method of claim 10, wherein the spatial parameter includes a proximity of the antenna to a patient.

13. The computer-implemented method of claim 10, wherein the sensor is further configured to interpret motion.

14. The computer-implemented method of claim 13, further comprising:

determining if at least one of a velocity or a speed of motion of the antenna was within a predetermined window based on the sensed spatial parameter over the period of time; and providing an indication that the at least one of a velocity or the speed of motion of the antenna was within a predetermined window based on the determination.

15. The computer-implemented method of claim 10, further comprising projecting a pattern of visible light on a patient by a light source, the pattern configured to indicate a proximity of the antenna to the patient.

16. The computer-implemented method of claim 10, wherein the scanning is performed for a predetermined period of time.

17. The computer-implemented method of claim 10, wherein the antenna includes at least two coils, and wherein the computer-implemented method further includes determining the spatial parameter of the antenna over a period of time based on the at least two coils.

18. A non-transitory computer-readable storage medium in which is stored instructions for causing a processor to execute a computer-implemented method for reducing variability in detecting and counting surgical items, the method comprising:

scanning, using an antenna, for an RFID tag, wherein the antenna is configured to receive a return signal transmitted by the RFID tag;

sensing, by a sensor, a signal indicative of a spatial parameter of an antenna over a period of time, wherein the sensor is configured to generate a signal indicative of a spatial parameter of the antenna when scanning for the RFID tag;

providing an indication that the spatial parameter of the antenna over time meets a predetermined rule;

determining if the antenna was moved in a predetermined scanning pattern based on the sensed spatial parameter over the period of time; and providing an indication that the antenna was moved in the predetermined scanning pattern based on the determination.

* * * * *